United States Patent
Kim et al.

(10) Patent No.: US 9,283,553 B2
(45) Date of Patent: Mar. 15, 2016

(54) HYDROCRACKING CATALYST FOR PREPARING VALUABLE LIGHT AROMATIC HYDROCARBONS FROM POLYCYCLIC AROMATIC HYDROCARBONS

(75) Inventors: Do Woan Kim, Daejeon (KR); Jae Hyun Koh, Daejeon (KR); Sang Il Lee, Daejeon (KR); Seung Woo Lee, Daejeon (KR); Seung Hoon Oh, Seoul (KR); Jae Suk Koh, Daejeon (KR); Yong Seung Kim, Seoul (KR); Gyung Rok Kim, Daejeon (KR); Sun Choi, Daejeon (KR); Hong Chan Kim, Jeju-si (KR); Sang Hun Oh, Gyeonggi-do (KR)

(73) Assignee: SK INNOVATION CO., LTD., Seoul (KR)

( * ) Notice: Subject to any disclaimer, the term of this patent is extended or adjusted under 35 U.S.C. 154(b) by 342 days.

(21) Appl. No.: 13/880,294

(22) PCT Filed: Oct. 21, 2011

(86) PCT No.: PCT/KR2011/007877
§ 371 (c)(1),
(2), (4) Date: Apr. 18, 2013

(87) PCT Pub. No.: WO2012/053853
PCT Pub. Date: Apr. 26, 2012

(65) Prior Publication Data
US 2013/0210611 A1 Aug. 15, 2013

(30) Foreign Application Priority Data

Oct. 22, 2010 (KR) .................. 10-2010-0103540

(51) Int. Cl.
| | | |
|---|---|---|
| *B01J 29/78* | (2006.01) | |
| *B01J 29/72* | (2006.01) | |
| *B01J 29/76* | (2006.01) | |
| *B01J 37/20* | (2006.01) | |
| *C07C 4/02* | (2006.01) | |
| *C10G 47/20* | (2006.01) | |

(52) U.S. Cl.
CPC .......... *B01J 29/7815* (2013.01); *B01J 29/7215* (2013.01); *B01J 29/7615* (2013.01); *B01J 37/20* (2013.01); *C07C 4/02* (2013.01); *C10G 47/20* (2013.01); *B01J 2229/42* (2013.01); *C07C 2529/74* (2013.01); *C07C 2529/76* (2013.01); *C07C 2529/78* (2013.01); *C10G 2300/1096* (2013.01); *C10G 2400/30* (2013.01); *Y02P 20/52* (2015.11)

(58) Field of Classification Search
CPC .......... B01J 23/28; B01J 23/75; B01J 23/882; B01J 27/0515; B01J 29/7007; B01J 29/7215; B01J 29/7615
USPC .............. 502/60, 220–222, 313; 423/DIG. 27
See application file for complete search history.

(56) References Cited

U.S. PATENT DOCUMENTS

| | | | |
|---|---|---|---|
| 4,913,798 A * | 4/1990 | Gortsema et al. ........ 208/111.15 |
| 5,128,024 A | 7/1992 | LaPierre et al. | |
| 5,139,984 A | 8/1992 | Iwamoto et al. | |
| 5,395,512 A | 3/1995 | Hsing et al. | |
| 6,524,470 B1 | 2/2003 | Kasztelan et al. | |
| 2002/0091060 A1* | 7/2002 | Cheng et al. ..................... 502/63 |
| 2004/0266608 A1* | 12/2004 | Long et al. ....................... 502/68 |
| 2006/0199725 A1 | 9/2006 | Du et al. | |
| 2007/0102321 A1 | 5/2007 | Wang | |
| 2007/0209969 A1 | 9/2007 | Shen et al. | |
| 2011/0042270 A1* | 2/2011 | Guillon et al. ................. 208/118 |
| 2011/0180455 A1* | 7/2011 | Bouchy et al. .................. 208/49 |

FOREIGN PATENT DOCUMENTS

| | | |
|---|---|---|
| CN | 101305078 A | 11/2008 |
| EP | 1900430 A1 | 3/2008 |
| WO | 2007055488 A1 | 5/2007 |

OTHER PUBLICATIONS

International Search Report for PCT/KR2011/007877 Dated May 1, 2012.
Office Action dated Apr. 3, 2014 issued by the Chinese Patent Office.
European Search Report for Application No. 06722404.8 dated Jan. 26, 2015.

* cited by examiner

*Primary Examiner* — Patricia L Hailey
(74) *Attorney, Agent, or Firm* — Abelman, Frayne & Schwab

(57) ABSTRACT

This invention relates to a hydrocracking catalyst for preparing valuable light aromatic hydrocarbons from polycyclic aromatic hydrocarbons derived from oil, which includes (i) beta-zeolite, (ii) pseudo-boehmite, and (iii) one or more metals selected from among metals of Groups VIII and VIB, and which further includes a cocatalyst component, thereby producing a maximum amount of BTX (Benzene, Toluene, Xylene) from LCO (Light Cycle Oil).

11 Claims, No Drawings

HYDROCRACKING CATALYST FOR PREPARING VALUABLE LIGHT AROMATIC HYDROCARBONS FROM POLYCYCLIC AROMATIC HYDROCARBONS

CROSS-REFERENCE TO RELATED APPLICATIONS

This application is a National Phase of PCT/KR2011/007877, filed 21 Oct. 2011, which claims priority from Korean Application No. 10-2010-0103540, filed 22 Oct. 2010, the disclosures of which are all incorporated herein by reference.

TECHNICAL FIELD

The present invention relates to a hydrocracking catalyst for preparing valuable light aromatic hydrocarbons from polycyclic aromatic hydrocarbons derived from oil.

BACKGROUND ART

Typically, polycyclic aromatic hydrocarbons, in particular, bicyclic aromatic hydrocarbons such as naphthalene and alkyl-substituted naphthalene, are the main constituents of inexpensive oils derived from oil. Furthermore, light aromatic hydrocarbons resulting from the hydrocracking of polycyclic aromatic hydrocarbons are generally known as C6~C13 hydrocarbons including benzene and alkyl-substituted benzene.

Meanwhile, polycyclic aromatic hydrocarbons are converted into light aromatic hydrocarbons using hydrocracking via the following reaction route. Specifically, in the case of a representative bicyclic aromatic hydrocarbon, that is, naphthalene, when hydrogen is added to naphthalene in the presence of a catalyst, one of the two benzene rings of naphthalene is hydrogenated, so that naphthalene is converted to tetralin one ring of which is a benzene ring and the other ring of which is a naphthene ring. The naphthene ring of the tetralin thus converted is continuously hydrocracked, ultimately obtaining a light aromatic hydrocarbon in which an alkyl group is substituted on the one benzene ring.

Although techniques for producing Benzene, Toluene, and Xylene (hereinafter, BTX) using a hydrocracking catalyst as in the present invention have been already disclosed, they are problematic because the maximum amount of BTX is unattainable. Hence, the production of a maximum amount of BTX from Light Cycle Oil (hereinafter, LCO) is required, and furthermore, increasing attention is being paid to a hydrocracking catalyst enabling such production.

DISCLOSURE OF INVENTION

Technical Problem

Under such circumstances, the present inventors have prepared valuable light aromatic hydrocarbons from polycyclic aromatic hydrocarbons derived from oil and furthermore have produced a hydrocracking catalyst enabling such preparation, and therefore the present invention has been devised in response to the need by the market for the above techniques.

Accordingly, an object of the present invention is to provide a novel hydrocracking catalyst for preparing valuable light aromatic hydrocarbons from polycyclic aromatic hydrocarbons.

Solution to Problem

In order to accomplish the above object, the present invention provides a hydrocracking catalyst for preparing valuable light aromatic hydrocarbons from polycyclic aromatic hydrocarbons derived from oil, comprising (i) beta-zeolite; (ii) pseudoboehmite; and (iii) one or more metals selected from among metals of Groups VIII and VIB, optionally containing one or more cocatalyst components selected from the group consisting of tin (Sn), phosphorus (P), boron (B), silicon (Si), bismuth (Bi), and lead (Pb).

Advantageous Effects of Invention

According to the present invention, there is provided a method which enables the production of valuable light aromatic hydrocarbons from polycyclic aromatic hydrocarbons derived from oil and the production of a maximum amount of BTX from LCO.

In particular, among a variety of hydrocracking catalysts, catalyst components are selectively included, so that a maximum amount of BTX can be produced from LCO.

Mode for the Invention

Hereinafter, a detailed description will be given of the present invention.

The present invention pertains to a hydrocracking catalyst for preparing valuable light aromatic hydrocarbons from polycyclic aromatic hydrocarbons derived from oil. According to the present invention, polycyclic aromatic hydrocarbons used as the feed are the main constituents of inexpensive oils, for example, LCO (Light Cycle Oil), derived from oil. In particular, bicyclic aromatic hydrocarbons such as naphthalene and alkyl-substituted naphthalene are mostly included but the present invention is not limited thereto. Any hydrocarbon including polycyclic aromatic materials that may be derived from oil may be used.

Also, valuable light aromatic hydrocarbons produced by hydrocracking polycyclic aromatic hydrocarbons are generally known as C6~C13 hydrocarbons including benzene and alkyl-substituted benzene. In particular, valuable light aromatic hydrocarbons include mainly BTX (Benzene, Toluene, Xylene).

The schematic reaction route for converting polycyclic aromatic hydrocarbons to light aromatic hydrocarbons via hydrocracking according to the present invention is described below.

Among polycyclic aromatic hydrocarbons, a representative bicyclic aromatic hydrocarbon, that is, naphthalene is illustratively described. In the case where hydrogen is added to naphthalene in the presence of a catalyst, one of two benzene rings that constitute the naphthalene is hydrogenated, so that the naphthalene is converted to tetralin one ring of which is a benzene ring and the other ring of which is a naphthene ring. The naphthene ring of the converted tetralin is continuously hydrocracked, resulting in a light aromatic hydrocarbon in which an alkyl group is substituted on one benzene ring.

Briefly, one or more among the benzene rings of a polycyclic aromatic hydrocarbon are saturated via hydrogenation and thereby the polycyclic aromatic hydrocarbon is converted to a hydrocarbon comprising one benzene ring and one or more naphthene rings, after which the naphthene rings are hydrocracked, thus obtaining a valuable light aromatic hydrocarbon.

As such, the reaction that produces BTX from naphthalene may cause a variety of side-reactions. Because products resulting from such side-reactions have no BTX, the side-reactions may malfunction to decrease the amount of BTX in the products. Hence, the side-reactions should be suppressed in order to maximize the BTX yield."

The following is an illustration of side-reactions that occur when the reaction of the present invention takes place.

The first is a thermodynamic equilibrium between tetralin and naphthalene. The conversion of naphthalene to tetralin is essential in order for BTX to be prepared from bicyclic aromatic materials such as naphthalene. This is because BTX is produced by hydrocracking tetralin. Typically, the equilibrium is known to be shifted toward tetralin in proportion to a decrease in temperature and an increase in pressure.

Also because the hydrocracking of the present invention is carried out under conditions of high temperature and high pressure, tetralin converted from naphthalene may be re-converted to naphthalene depending on the reaction conditions. In order to prevent the re-conversion to naphthalene, the process conditions should be changed in such a manner that the reaction temperature is lowered by as much possible and the reaction pressure is increased, or the converted tetralin should be rapidly hydrocracked to thus produce BTX, whereby the concentration of tetralin in the feed is lowered and the conversion of tetralin to naphthalene is thus reduced. The hydrocracking performance of the hydrocracking catalyst according to the present invention is high and thus the re-conversion to naphthalene may be minimized, thereby maximizing the production of BTX.

The second is a conversion of tetralin to decalin in which one benzene ring of the tetralin is additionally hydrogenated and thus both of two rings are saturated. The decalin produced in the presence of hydrogen at high pressure may be converted to paraffin via additional hydrocracking. When such a side-reaction occurs to a great extent, the amount of BTX in the product may be decreased.

Actually, in the case where a hydrocracking reaction of the present invention is performed using a hydrotreating catalyst having high hydrogenation activity, the amount of naphthene or paraffin produced is larger than that of BTX. To suppress such a side-reaction, the hydrogenation activity of the hydrocracking catalyst should be appropriately controlled so that the hydrogenation reaction for producing tetralin from naphthalene is promoted and the hydrogenation reaction for producing decalin from tetralin is suppressed. Briefly, when the hydrogenation activity of the hydrocracking catalyst according to the present invention is properly controlled, the production of naphthene and paraffin may be minimized and the production of BTX may be maximized.

The third is an additional hydrogenation of BTX resulting from hydrocracking of tetralin, undesirably converting the BTX to cyclohexane-like naphthene. The produced naphthene may be converted to paraffin via additional hydrocracking. This side-reaction may take place when the hydrogenation activity of the hydrocracking catalyst is very strong, as in the second side-reaction as above. That is, the hydrogenation activity of the hydrocracking catalyst according to the present invention is controlled such that the additional hydrogenation of the produced BTX is suppressed, thereby maximizing the production of BTX.

In order to prepare valuable light aromatic hydrocarbons from polycyclic aromatic hydrocarbons, a hydrocracking catalyst is required. The hydrocracking catalyst according to the present invention includes (i) beta-zeolite; (ii) pseudo-boehmite as a binder; and (iii) one or more metals selected from among metals of Groups VIII and VIB, optionally containing one or more cocatalyst components selected from the group consisting of tin (Sn), phosphorus (P), boron (B), silicon (Si), bismuth (Bi), and lead (Pb).

In particular, the metal of Group VIII of the hydrocracking catalyst may be cobalt, and the metal of Group VIB may be molybdenum. Moreover, the cobalt or molybdenum component may be provided in the form of a sulfide. This is considered to be because the sulfidation of a metal oxide having no hydrogenation activity may result in appropriate hydrogenation activity and high resistance to poisoning caused by sulfur and nitrogen compounds present in the feed.

Furthermore, the cocatalyst component of the hydrocracking catalyst according to the present invention may be tin (Sn). In the case where tin (Sn) is used, it may interact with the active metal of the hydrocracking catalyst, namely, cobalt or molybdenum, thus controlling the hydrogenation activity of cobalt or molybdenum, thereby increasing the BTX yield.

The total Si/Al atom ratio of beta-zeolite that constitutes the hydrocracking catalyst falls in the range of 5~200, thus providing the cracking function of the hydrocracking catalyst necessary for production of BTX, particularly favored being 10~150.

In the hydrocracking catalyst, beta-zeolite exists in the form of an extrudate mixed with pseudo-beohmite as the binder, and the amount of beta-zeolite in the extrudate may be 10~95 wt % based on the total weight of the catalyst in order to maintain the mechanical strength of a support and ensure the cracking function of the hydrocracking catalyst necessary for production of BTX, particularly favored being 30~90 wt %.

The amount of cobalt or molybdenum may be 0.1~20 wt % based on the total weight of the catalyst in order to ensure the hydrogenation activity of the hydrocracking catalyst for maximally producing BTX, particularly favored being 1~10 wt %.

Also the amount of tin (Sn) may be 0.01~10 wt % based on the total weight of the catalyst in order to modify the hydrogenation activity of the hydrocracking catalyst via interaction with cobalt or molybdenum, particularly favored being 0.5~5 wt %.

In the hydrocracking catalyst, when cobalt or molybdenum is used as the main catalyst and tin is used as the cocatalyst and these are added in amounts less than the above lower limits, the number of active sites of the catalyst may be decreased, undesirably deteriorating the hydrogenation performance, resulting in lowered BTX yield.

In contrast, when cobalt or molybdenum is the main catalyst and tin is the cocatalyst and these are added in amounts larger than the above upper limits, cobalt or molybdenum which is the active metal and tin may be sintered, so that the number of active sites is similar compared to when using a hydrocracking catalyst within the above ranges, thus exhibiting a similar BTX yield or blocking the pores of beta-zeolite by the sintered particles, undesirably deteriorating the hydrogenation performance.

In order to additionally explain the principle of the present invention, examples are given below, but the intent of the present example is not to limit the scope of the present invention as envisioned by the present inventors.

EXAMPLE

Comparison of Performance of Various Transition Metal Sulfide Catalysts

Example 1

Preparation of Co-BETA Catalyst

A catalyst comprising beta-zeolite having a diameter of 1 mm (zeolite:binder=7:3, weight ratio) and about 5 wt % of cobalt (Co) was prepared. The cobalt precursor used was cobalt nitrate hexahydrate (hereinafter, CNH). (Cobalt may be provided as a variety of precursors and is not limited only to the above precursor.)

The above catalyst was prepared in the following procedures.

Specifically, CNH was first dissolved in distilled water thus obtaining a CNH aqueous solution with which beta-zeolite was then impregnated, followed by performing drying at 150° C. for 2 hours and continuous calcination at 500° C. for 2 hours, thereby preparing a Co-BETA catalyst.

Example 2

Preparation of Mo-BETA Catalyst

This catalyst was prepared in the same manner as in Example 1, with the exception that ammonium heptamolybdate was used instead of CNH. (Mo may be provided as a variety of precursors and is not limited only to the above precursor.)

Comparative Example 1

Preparation of Pt-BETA Catalyst

This catalyst was prepared in the same manner as in Example 1, with the exception that hydrogen hexachloroplatinate was used instead of CNH. (Pt may be provided as a variety of precursors and is not limited only to the above precursor.)

Comparative Example 2

Preparation of Pd-BETA Catalyst

This catalyst was prepared in the same manner as in Example 1, with the exception that palladium nitrate hydrate was used instead of CNH. (Pd may be provided as a variety of precursors and is not limited only to the above precursor.)

Comparative Example 3

Preparation of Fe-BETA Catalyst

This catalyst was prepared in the same manner as in Example 1, with the exception that iron nitrate was used instead of CNH. (Fe may be provided as a variety of precursors and is not limited only to the above precursor.)

The catalysts thus prepared were sulfide using the following method, and then used in hydrocracking reaction. The results are shown in Table 1 below.

—Sulfidation of Catalyst—

To 5 cc of the catalyst prepared in each of the above examples and comparative examples described to additionally explain the principle of the present invention, R-LGO including DMDS as a feed for sulfidation was allowed to flow at a rate of 0.08 cc/min under conditions of a pressure of 50 bar and hydrogen supply of 90 cc/min, and the catalyst was heated to 232° C. and maintained at 232° C. for 6 hours, after which the catalyst was heated to 320° C. and maintained at 320° C. for 6 hours, so that the catalyst was sulfided.

—Hydrocracking Reaction—

After all of the catalysts of the above examples and comparative examples were sulfide as the above method, reaction conditions including a pressure of 80 bar and hydrogen supply of 90 cc/min were set, and then the reaction temperature was increased to 410° C. Thereafter, tetralin as a feed was allowed to flow at a rate of 0.08 cc/min, so that hydrocracking was carried out. After the steady-state was achieved, the reaction product was recovered at intervals of 8 hours to analyze components in the product using GC-MSD. The performance of the catalysts was compared based on the conversion of tetralin as the feed, the amount of monocyclic aromatic hydrocarbon having no naphthene ring in the liquid product, and the amount of C6~C8 aromatic hydrocarbon such as BTX in the liquid product.

Tetralin conversion (%)=(100 amount of tetralin in product)/100*100

TABLE 1

| Catalyst | Tetralin Conversion (%) | Amount of Monocyclic Aromatic Hydrocarbon without Naphthene Ring (%) | Amount of BTX (%) |
|---|---|---|---|
| Ex. 1 | 99 | 93 | 83 |
| Ex. 2 | 99 | 92 | 84 |
| C. Ex. 1 | 99 | 40 | 32 |
| C. Ex. 2 | 79 | 52 | 27 |
| C. Ex. 3 | 60 | 32 | 22 |

Comparison of Performance of Hydrocracking Catalysts with Respect to Amount of Co Example 3

Preparation of 1 wt % Co-BETA Catalyst

This catalyst was prepared in the same manner as in Example 1, with the exception that the amount of Co was 1 wt % based on the total weight of the catalyst.

Example 4

Preparation of 3 wt % Co-BETA Catalyst

This catalyst was prepared in the same manner as in Example 1, with the exception that the amount of Co was 3 wt % based on the total weight of the catalyst.

Example 5

Preparation of 10 wt % Co-BETA Catalyst

This catalyst was prepared in the same manner as in Example 1, with the exception that the amount of Co was 10 wt % based on the total weight of the catalyst.

Example 6

Preparation of 20 wt % Co-BETA Catalyst

This catalyst was prepared in the same manner as in Example 1, with the exception that the amount of Co was 20 wt % based on the total weight of the catalyst.

Comparative Example 4

Preparation of 30 wt % Co-BETA Catalyst

This catalyst was prepared in the same manner as in Example 1, with the exception that the amount of Co was 30 wt % based on the total weight of the catalyst.

TABLE 2

| Catalyst | Tetralin Conversion (%) | Amount of Monocyclic Aromatic Hydrocarbon without Naphthene Ring (%) | Amount of BTX (%) |
|---|---|---|---|
| Ex. 1 | 99 | 93 | 83 |
| Ex. 3 | 87 | 87 | 77 |
| Ex. 4 | 95 | 89 | 80 |
| Ex. 5 | 98 | 92 | 81 |
| Ex. 6 | 96 | 82 | 75 |
| C. Ex. 4 | 73 | 70 | 65 |

Comparison of Performance of Hydrocracking Catalysts Using Various Zeolites

Comparative Example 5

Preparation of Co-USY Catalyst

This catalyst was prepared in the same manner as in Example 1, with the exception that USY zeolite was used instead of beta-zeolite.

Comparative Example 6

Preparation of Co—SiO$_2$—Al$_2$O$_3$ Catalyst

This catalyst was prepared in the same manner as in Example 1, with the exception that amorphous SiO$_2$—Al$_2$O$_3$ was used instead of beta-zeolite.

TABLE 3

| Catalyst | Tetralin Conversion (%) | Amount of Monocyclic Aromatic Hydrocarbon without Naphthene Ring (%) | Amount of BTX (%) |
|---|---|---|---|
| Ex. 1 | 99 | 93 | 83 |
| C. Ex. 5 | 97 | 65 | 42 |
| C. Ex. 6 | 67 | 36 | 21 |

Comparison of Performance of Hydrocracking Catalysts Including Cocatalyst

Example 7

Preparation of Co—Sn-BETA Catalyst

CNH and tin chloride were dissolved in distilled water so that the amounts of Co and Sn were respectively 5 wt % and 3 wt % based on the total weight of the catalyst, and then beta-zeolite was impregnated with the resultant aqueous solution, followed by drying at 150° C. for 2 hours and continuous calcination at 500° C. for 2 hours, thus preparing a Co—Sn-BETA catalyst. (Co and Sn may be provided as a variety of precursors and are not limited only to the above precursors.)

Example 8

Preparation of Mo—Sn-BETA Catalyst

This catalyst was prepared in the same manner as in Example 7, with the exception that ammonium heptamolybdate was used in lieu of CNH.

Comparative Example 7

Preparation of Co—Cr-BETA Catalyst

This catalyst was prepared in the same manner as in Example 7, with the exception that chromium (III) nitrate was used in lieu of tin chloride. (Cr may be provided as a variety of precursors and is not limited only to the above precursor.)

Comparative Example 8

Preparation of Co—Ni-BETA Catalyst

This catalyst was prepared in the same manner as in Example 7, with the exception that nickel nitrate was used in lieu of tin chloride. (Ni may be provided as a variety of precursors and is not limited only to the above precursor.)

TABLE 4

| Catalyst | Tetralin Conversion (%) | Amount of Monocyclic Aromatic Hydrocarbon without Naphthene Ring (%) | Amount of BTX (%) |
|---|---|---|---|
| Ex. 7 | 99.5 | 96 | 85 |
| Ex. 8 | 99.5 | 94 | 85 |
| C. Ex. 7 | 91 | 62 | 44 |
| C. Ex. 8 | 92 | 62 | 47 |

Comparison of Performance of Hydrocracking Catalysts with Respect to Amount of Cocatalyst

Example 9

Preparation of Co—Sn-BETA (Sn: 1 wt %) Catalyst

This catalyst was prepared in the same manner as in Example 7, with the exception that the amount of Sn was 1 wt % based on the total weight of the catalyst.

Comparative Example 9

Preparation of Co—Sn-BETA (Sn: 20 wt %) Catalyst

This catalyst was prepared in the same manner as in Example 7, with the exception that the amount of Sn was 20 wt % based on the total weight of the catalyst.

TABLE 5

| Catalyst | Tetralin Conversion (%) | Amount of Monocyclic Aromatic Hydrocarbon without Naphthene Ring (%) | Amount of BTX (%) |
|---|---|---|---|
| Ex. 1 | 99 | 93 | 83 |
| Ex. 7 | 99.5 | 96 | 85 |
| Ex. 9 | 99.5 | 94 | 83 |
| C. Ex. 9 | 60 | 36 | 17 |

Although the embodiments of the present invention have been disclosed for illustrative purposes, those skilled in the art will appreciate that a variety of different modifications and substitutions are possible, without departing from the scope and spirit of the invention as disclosed in the accompanying claims. Accordingly, such modifications and substitutions should also be understood as falling within the scope of the present invention.

The invention claimed is:

1. A hydrocracking catalyst for preparing light aromatic hydrocarbons from polycyclic aromatic hydrocarbons, comprising:
   (i) beta-zeolite;
   (ii) pseudo-boehmite;
   (iii) one or more metals selected from the group consisting of cobalt and molybdenum,
   (iv) cocatalyst comprising 0.01-10 wt % of tin (Sn) based on a total weight of the catalyst.

2. The hydrocracking catalyst of claim 1, wherein cobalt or molybdenum is in the form of a sulfide.

3. The hydrocracking catalyst of claim 1, wherein a total Si/Al atom ratio of the beta-zeolite is in a range of 5-200.

4. The hydrocracking catalyst of claim 3, wherein the total Si/Al atom ratio of the beta-zeolite is in the range of 10-150.

5. The hydrocracking catalyst of claim 1, wherein an amount of the beta-zeolite is 10-95 wt % based on a total weight of the catalyst.

6. The hydrocracking catalyst of claim 5, wherein the amount of the beta-zeolite is 30-90 wt % based on the total weight of the catalyst.

7. The hydrocracking catalyst of claim 1, wherein an amount of cobalt is 0.1-20 wt % based on a total weight of the catalyst.

8. The hydrocracking catalyst of claim 7, wherein an amount of cobalt is 1-10 wt % based on a total weight of the catalyst.

9. The hydrocracking catalyst of claim 1, wherein the amount of tin is 0.5-5 wt % based on the total weight of the catalyst.

10. The hydrocracking catalyst of claim 1, wherein the amount of molybdenum is 0.1-20 wt % based on a total weight of the catalyst.

11. The hydrocracking catalyst of claim 10, wherein the amount of molybdenum is 1-10 wt % based on the total weight of the catalyst.

* * * * *